United States Patent [19]

Shoesmith

[11] Plant 5,043

[45] Apr. 26, 1983

[54] CHRYSANTHEMUM NAMED TWILIGHT

[75] Inventor: Leonard H. Shoesmith, Westfield-Woking, England

[73] Assignee: Pan American Plant Company, Parrish, Fla.

[21] Appl. No.: 313,933

[22] Filed: Oct. 22, 1981

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A new and distinct daisy chrysanthemum particularly suitable for year round pot plant production as a nine-week medium, this plant being characterized by a profuse production of medium sized flowers of a pleasing pink color displayed in a mound over an abundant production of foliage.

4 Drawing Figures

BACKGROUND OF THE NEW PLANT

This plant was discovered in 1977 at West Chicago, Ill., growing as a seedling of unknown parentage among a group of miscellaneous seedlings which were originated by me and grown for observation in the hope of finding new and interesting varieties suitable for the commercial market. The profuse production of flowers having a delightful pink coloration caused it to be selected for propagation and testing. Extensive propagation by cuttings, under my direction and through successive generations, has shown that this new plant is particularly suitable for four-inch pot plant culture having generally a nine-week response. The culture of this new plant through many successive generations has shown that its novel characteristics hold true and appear to be firmly fixed. Commercial scale propagation of this new plant is now being carried on at Parrish and Cortez, Fla., as well as at West Chicago, Ill.

DESCRIPTION OF THE DRAWINGS

This new chrysanthemum cultivar is illustrated by the accompanying drawings, of which sheet one is a full color photographic rendition of a potted plant in full bloom; sheet two is a photographic close-up view of flowers of this new plant which has been hand-painted to show the true color of the blooms; sheet three is a machine copy of a photoprint showing the top side of typical leaves of this new variety; and sheet four is a machine copy of a photoprint rendition of the same leaves but showing the bottom side thereof.

DESCRIPTION OF THE NEW PLANT

The following is a detailed description of my new chrysanthemum variety based upon observations made in the Spring of 1981 of plants grown in greenhouse at West Chicago, Ill., the color designations being according to The R.H.S. Colour Chart published by The Royal Horticultural Society of London, England.

THE PLANT

Origin: Seedling.
Parentage: Unknown.
Classification:
*Botanic.*—*Chrysanthemum morifolium.*
*Commercial.*—Pot chrysanthemum.

Form: Perennial bush of upright shape with normal branching characteristics.
Height: Medium, varying according to environmental circumstances.
Growth: Vigorous, strong and upright.
Foliage:
*Quantity.*—Abundant.
*Size of leaf.*—Up to about 70 mm. long and about 60 mm. wide.
*Shape.*—Ovate with cleft margins.
*Texture.*—Leathery.
*Venation.*—Pinnate.
*Color.*—Upper side — 147A. Under side — 147B.
*Petioles.*—Length — About 10 mm.
*Rachis.*—Up to about 70 mm. long.

THE BUD

Form: Globular.
Size: The size varies in both diameter and length.
Opening rate: Variable depending upon environmental temperature.
Color of florets:
*When phyllaries first divide.*—70B.
*When petals begin to unfurl.*—70B.
Phyllaries:
*Number.*—About 15.
*Shape.*—Lanceolate.
*Color.*—138C.
Peduncle:
*Character.*—Erect and rigid.
*Aspect.*—Pubescent.
*Color.*—138C.

THE FLOWER

Blooming habit: Intermittent, blooming once and profusely in the Fall.
Blooms:
*Size.*—Medium. Diameter — About 45 to 65 mm. Depth — Flat.
Borne: Singly.
Form: A single (daisy) composite inflorescence borne on a receptacle surrounded by an involucre of bracts.
Shape:
*When bloom first opens.*—Cup-shaped.
*When bloom matures.*—Flat.
Petalage:
*Ray florets.*—About 20 in number.
*Disc florets.*—Numerous.

*Arrangement.*—Imbricated.

*Form.*—Elliptic with rounded apex and entire margins.

Texture: Soft.

Appearance: Satiny.

Color:

*Ray florets.*—Upper side — 70B. Under side — 70D.

*Disc florets.*—Yellow. The color of the ray florets varies with temperature and light intensity. Normally the color is a darker pink as the bloom becomes fully opened and fades evenly to 77C as the bloom fully matures.

Peduncle:

*Character.*—Strong and upright.

*Length.*—Variable.

*Color.*—138C.

Persistence: The flowers hang on and dry.

Fragrance: Typical chrysanthemum.

Lasting quality: About three weeks on the plant.

REPRODUCTIVE ORGANS

Stamens:

*Number.*—Five.

*Arrangement.*—Syngenesious.

*Anthers.*—Yellow in color and of insignificant size.

*Filaments.* —Color and length are insignificant.

*Pollen.*—Color — Yellow.

Pistils:

*Number.*—One for each floret.

*Styles.*—The length is insignificant. The color is yellow.

Stigmas:

*Color.*—Yellow.

Ovaries: Inferior and bicarpellate.

This plant most nearly resembles "Circus" (U.S. Plant Pat. No. 4,188). It is generally shorter and has fewer breaks than "Circus", but is less affected by extreme temperatures.

I claim:

1. A new and distinct chrysanthemum cultivar, substantially as herein shown and described, characterized by its profuse production of distinct pink daisy-type flowers of medium size and good substance, and its adaptability for year round pot plant production.

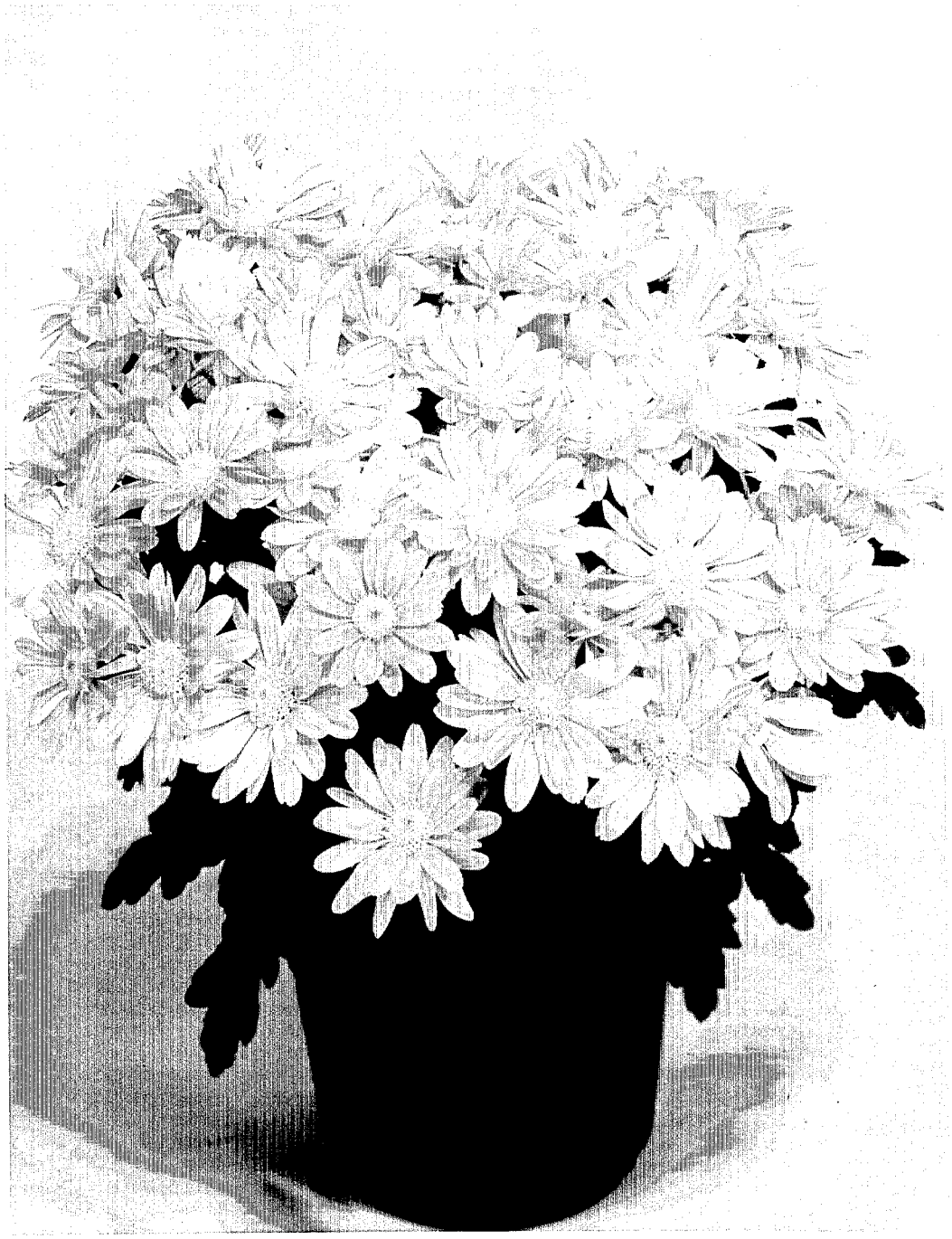

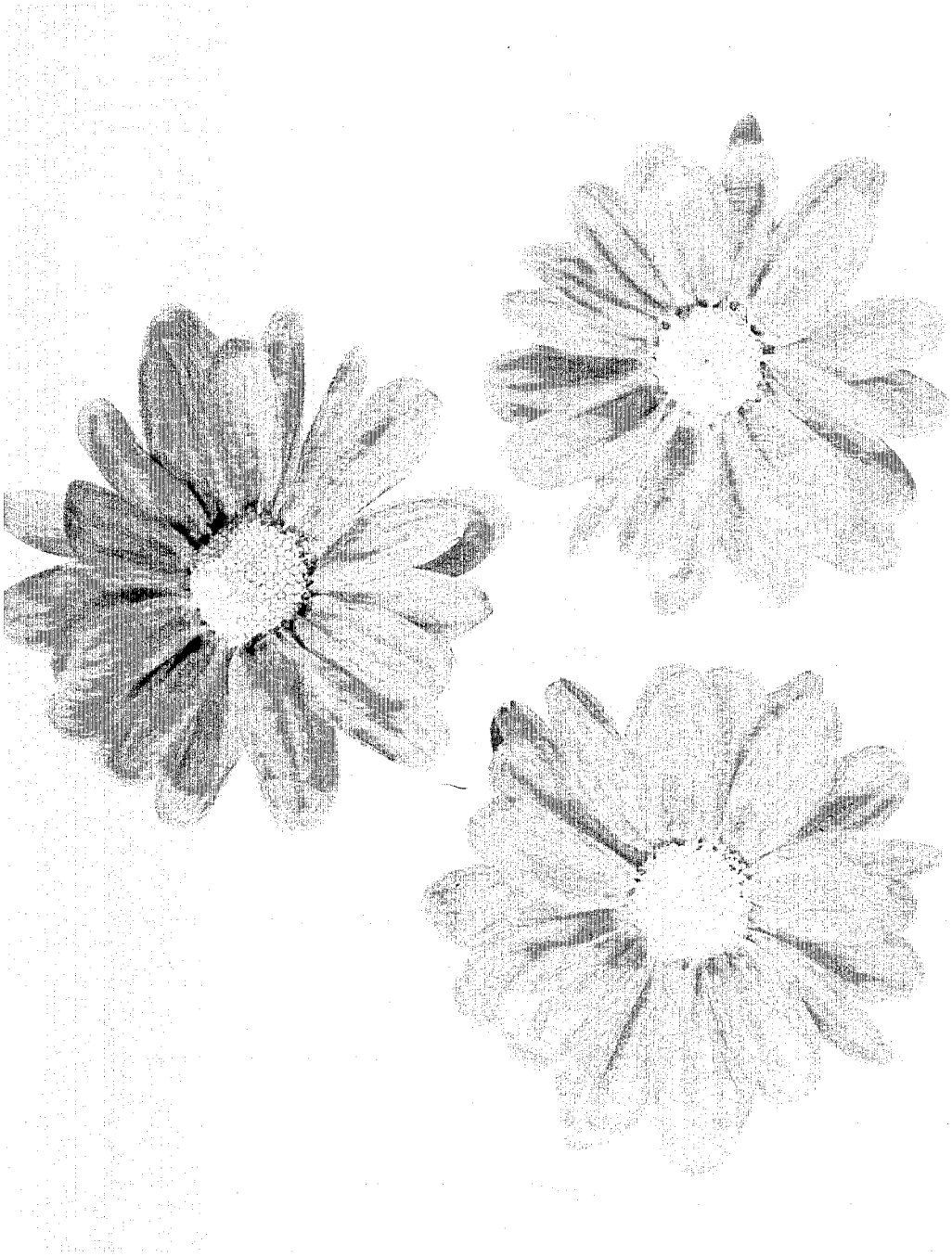

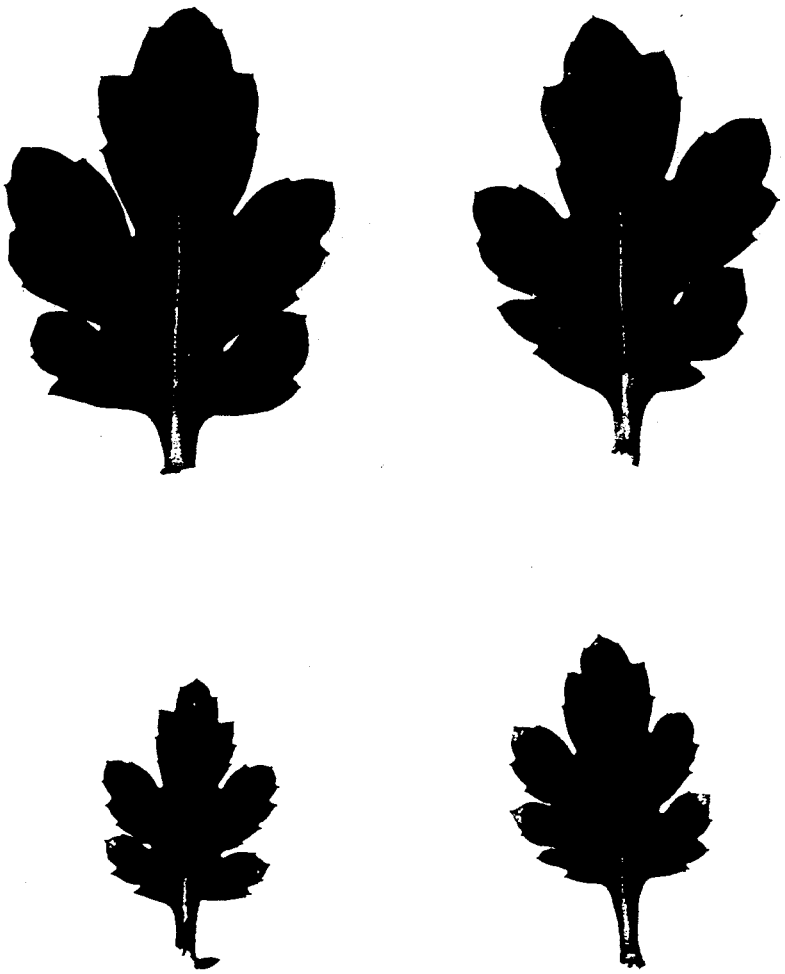

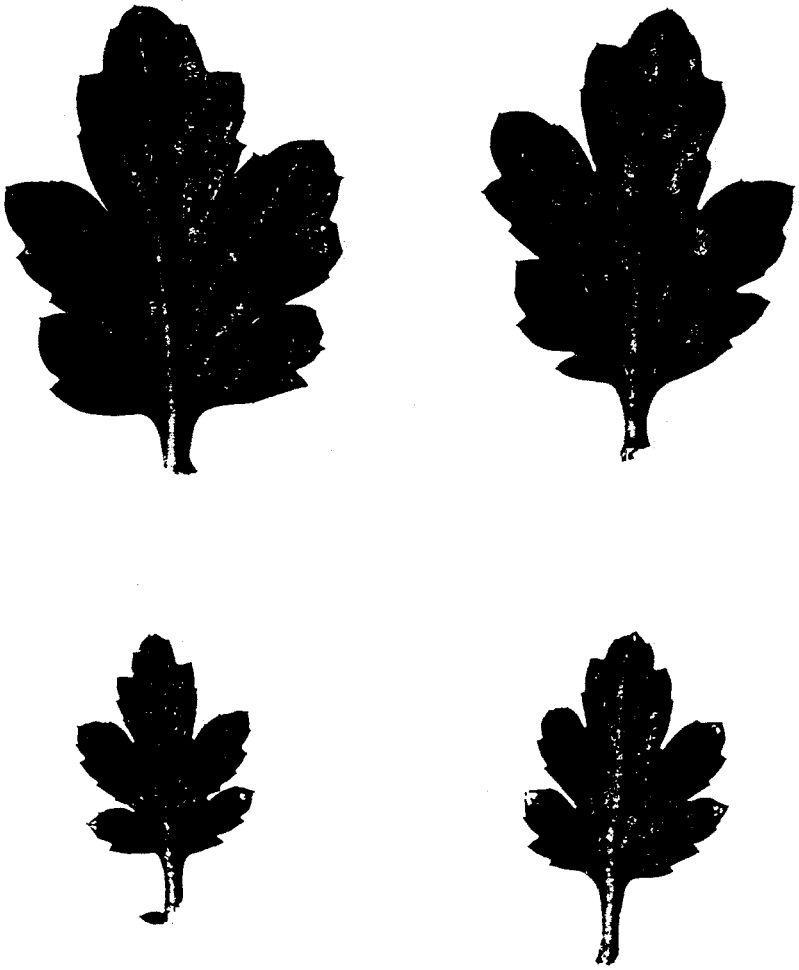

* * * * *